US005523292A

United States Patent [19]
Schwartz et al.

[11] Patent Number: 5,523,292
[45] Date of Patent: Jun. 4, 1996

[54] METHOD OF PREVENTING RESTENOSIS FOLLOWING CORONARY ANGIOPLASTY

[76] Inventors: Robert Schwartz, 1123 Audaz La. SW., Rochester, Minn. 55902; Robert A. O'Brien, 251 Vreeland Ave., Nutley, N.J. 07110

[21] Appl. No.: 960,997

[22] Filed: Oct. 14, 1992

[51] Int. Cl.$^6$ .......................... A61K 38/16; A61K 38/17; C07K 14/435; C07K 14/46
[52] U.S. Cl. .................................. 514/21; 514/8; 514/822; 530/350; 530/395; 530/855; 530/856
[58] Field of Search ................................. 514/8, 21, 822; 530/350, 395, 855, 856

[56] References Cited

FOREIGN PATENT DOCUMENTS 0395375  10/1990  European Pat. Off. .
4041570  6/1992  Germany .

OTHER PUBLICATIONS

Canadian Journal of Surgery, vol. 33, No. 3, 1990, Toronto, pp. 207–210 Cole, C. W. et al "Heparin–Associated Thrombocytopenia and Thrombosis:Optimal Therapy with Ancrod", p. 208, col. 3, results.
Journal of Nuclear Medicine, vol. 33, No. 5, May 1992, New York, pp. 845–856 Schwartz R. S. et al. "Fibrin Deposition Following Coronary Artery Injury" Quantitation by I–125 Fibrinogen in a Porcine Restenosis Model.
"The Restenosis Paradigm Revisited: An Alternative Proposal for Cellular Mechanisms", Robert S. Schwartz et al, JACC vol. 20, No. 5, Nov. 1, 1992:1284–93.
"Use of Defibrinating Agents Ancrod and Reptilase in the Treatment of Thromboembolism"; H Kwann; pp. 239–251, 1973.
"Therapeutic Defibrination in the Treatment of Thrombotic Disease"; W. R. Bell; pp. 490–493, 1968.
"Blood Fibrinolytic Activity during Arvin Therapy"; W. R. Pitney et al; pp. 165–171, 1969.
"Prolonged Coagulation Defect (Defibrination Syndrome) in Malayan Viper Bite"; pp. 621–626; 1963.
"The Isolation and Properties of the Thrombin–like Activity from Ancistrodon Rhodostoma Venom"; M. P. Esnauf et al; pp. 582–590, 1967.
"Direct Effect of Fibrinogen–clotting Enzymes on Plasminogen Activator Secretion from Human Endothelial Cells"; T. Soszka et al; Thrombosis and Haemostasis 54: 164, 1985.
"Effects of Ancrod: Normalization of Fibrinolytic Enzyme Abornmalities in Patients with SLE and Lupus Nephritis".; P. Glas–Greenwalt et al; J Lab Clin Med 105: No. 1, 99–107, 1985.
"Lupus Nephritis with Thrombosis and Abnormal Fibrinolysis: Effect of Ancrod Therapy"; K. S. Kant et al; J Lab Clin Med 105: No. 1, 77–88, 1985.
"The Effect of Arvin on Blood Coagulating Factors"; W. Bell et al; Brit J. Haemat. 15, pp. 589–602, 1968.
"The Action of Arvin on Fibrin Stabilizing Factor (factor XIII)"; G. H. Barlow et al; Res Comm Chem Path Pharm 1: 39–42, 1970.

"Arvin in Peripheral Arterial Circulatory Disorders. Controlled Multicenter Trials"; G. K. Wolf; Europ. J. Clin Pharmacol 9: 387–392, 1976.
"Controlled Defibrination in the Treatment of Peripheral Vascular Disease"; J. A. Dormandy et a;; Angiology 29: 80–88, 1978.
"The Effects of Ancrod, the Coagulating Enzyme from the Venom of Malayan Pit Viper (A. rhodostoma) on Prothrombin and Fibrinogen Metabolism and Fibrinopeptide A Release in Man"; W. R. Bell; J Lab Clin Med 91: 592–604, 1978.
"In Vivo Effects of Agkistrodon Rhodostoma Venom. Studies with Fibrinogen"; E. Regoeczi et al; I. J. Clin Invest 45: 1202–1212, 1966.
"Defibrinogenating Enzymes"; W. R. Bell; Chapter 45 from Colman R, et al (Eds). Hemostasis and Thrombosis. J. B. Lippincott. Phila; pp. 886–900, 1987.
"Isotopic Studies of Therapeutic Coagulation with a Coagulating Enzyme"; W. Bell; J. Clin Invest 49: 1872–1879, 1970.
"Possible Pathway for Formation of Fibrin Degradation Products During Ancrod Therapy"; C. McKillop et al; Nature (London) 255: 638–639, 1975.
"Anticoagulant Therapy with a Purified Fraction of Malayan Pit Viper Venom"; A. A. Sharp et al; Lancet 1: 493–99, 1968.
"Deficiency of a Plasma Factor Stimulating Vascular Prostacyclin Generation in Patients with Lupus Nephritis and Glomerular Thrombi and its Correction by Ancrod": In–vivo and in–vitro Observations; K. S. Kant et al; Thromb Res 27: 651–58, 1982.
"The Laboratory Investigation of Fibrinolysis". In: Coagulation and Hemostais; G. Lower et al; Thompson J (ed). Churchill–Livingston., Edinburgh 222–260, 1980.
"The Place of Thrombolytic and Defibrinating Agents in the Treatment of Venous Thromboembolism": In: Thromboembolism: Advances in Etiology, Prevetnion, and Management.; H. Kwaan et al; Advances in Etiology, Prevetnion, and Management. Nicholaides A (Ed.). MTP Medical Publ. Lancaster, England, 251–267, 1975.
"Fibrinolysis in Vivo Predicts a Favorable Outcome in Patients with Glomerular Thrombi During Treatment with Ancrod"; S. Kant et al; The Seoul Journal of Medicine, vol. 29, No. 2: 155–165, Jun. 1988.
"Production of the Generalized Shwartzman Reaction in Rabbits by Ancrod ('Arvin') Infusion and Endotoxin Injection"; C. Krishnamurti et al; Brit. J. Maemat 25: 111–122, 1973.
"Precipitation of Ancrod–Induced Soluble Fibrin by Aprotinin and Norepinephrine"; Muller–Berghaus et a;; Thrombosis Research 2: 305–322, 1973.
"The Effect of Intraperitoneal Malayan Pit Viper Venom on Adhesion and Peritoneal Healing"; E. C. Ashby et al; Brit U. Surg. 57: 863, 1970.

(List continued on next page.)

Primary Examiner—Mindy Fleisher
Assistant Examiner—Nancy J. Degen

[57] ABSTRACT

The present invention comprises a method of alleviating restenosis, post-PTCA or other coronary arterial intervention, and more particularly, to the use of ancrod to prevent restenosis in the coronary arteries.

12 Claims, No Drawings

OTHER PUBLICATIONS

"Acquired Resistance to Treatment with Arvin"; W. Pitney et al; Lancet 1: 79–81, 1969.

"In Vivo Behavior of the Coagulant Enzyme from Agkistrodon Rhodostroma Venom: Studies Using I–Arvin"; E. Regoeczi et al; Br J. Maemat 16: 573, 1969.

"Effect of a Fibrinolytic Agent (Arvin) on Wound Healing and Collagen Formation"; P. J. L. Holt et al, Heberden Society, p. 335. No date given.

"Effects of Arvin in Mice"; Simone Silberman et al; Experimental and Molecular Pathology 14, 67–74, 1971.

"Pharmacology and Toxicology of a Defibrinating Substance from Malayan Pit Viper Venom"; A. Ashford et al; Pharmacology Department, Twyford Laboratories Limited, London N.W. 10. The Lancet pp. 486–489 1968.

"Experimental Arterial Thromboembolism in Baboons"; Laurence A. Harker et al; The American Society for Clinical Investigation, Inc.; vol. 64, Aug. 1979, pp. 559–569.

"Stimulation of Fibrinogen Synthesis by Thrombin in Rabbits with Ancrod–Induced Afibrinogenenmia"; Barbara M. Alving et al; Amer. J. Physiol. Now, vol. 233: 562–567, 1977.

"Effects of Ancrod (Arvin) in Mice: Studies of Plasma Fibrinogen and Fibrinolytic Activity", Simone Silberman et al; British Journal of Haematology, 1973, 24, 101.

"Fibrinogen–Independent Release of Plasminogen Activator in Ancrod–Treated Rabbits"; C. Krishnamurti et al; Thrombosis and Haemostasis 54: 170 (abstract), 1985.

"The Effect of Arvin Upon Cardiac Function"; M. Klein et al; Proceedings of the Society for Experimental Biology and Medicine, vol. 132: 1123–1126, 1969.

"Comparison of Ancrod and Heparin as Anticoagulants Following Endarterectomy in the Dog"; T. M. Daniel et al; Ann. Surg. August: 223–228, 1976.

"Arvin Treatment for Sickle–Cell Crisis"; The Lancet, pp. 542–543, Sep. 7, 1968.

"Streptokinase in Acute Myocardial Infarction"; The New England Journal of Medicine, vol. 301, No. 15, Oct. 11, 1979, pp. 797–802.

"Plasminogen Activator Inhibitor: A Physiologic Regulator of Fibrinolysis"; C. Krishmaurti; AFCR Hematology, Clinical Research, vol. 34, No. 2, 1986.

"Ancrod Enhances the Thrombolytic Effect of Urokinase and Recombinant Tissue–Type Plasminogen Activator"; Abstracts, JACC, vol. 9, No. 2, Feb. 1987.

"Controlled Trail of Ancrod and Heparin in Treatment of Deep–Vein Thrombosis of Lower Limb"; Davies et al; The Lancet, Jan. 15, 1972, pp. 113–115.

"Subcutaneous Ancrod in Prevention of Deep Vein Thrombosis After Hip Replacement Surgery"; Belch et al; Thrombosis Research 25; 23–31, 1982.

"Treatment of Central Retinal Vein Thrombosis with Ancrod"; Bowell et al; The Lancet, Jan. 24, 1970, pp. 173–174.

"Central Retinal Vein Thrombosis", Gent et al; Thrombosis Research 14; 61–66. 1979.

"Low–Dosage Ancrod for Prevention of Thrombotic Complications after Surgery for Fractured Neck of Femur", Barrie et al; British Medical Journal, Oct. 19, 1974, pp. 130–133.

"Subcutaneous Ancrod after Operation for Fractured Hip—a Dose–Ranging and Feasibility Study"; Lowe et al; Thhrombos. Haemostas., 1978.40, pp. 134–143.

"Controlled Trial of Ancrod in Ischemic Stroke"; Hossmann et al; Arch Neurol—vol. 40, Dec. 1983, pp. 803–808.

"Defibrinogenation with Arvin in Thrombotic Disorders"; W. R. Bell. 1974.

"Clinical Effects of Bites by Malayn Viper"; Reid et al; The Lancet, Mar. 23, 1963, pp. 617–621.

"The Proteolytic Action of Arvin on Human Fibrinogen"; Ewart et al; Biochem. J. (1970) 118, 603–609.

"Characterization of Peptides Released from Human Fibrinogen by Arvin"; Biochim. Biophys. Acta, 200 (1970) 587–589.

"The Mechanism of Action of Arvin and Reptilase"; Kwaan et al; pp. 361–368. No date given no source given.

"The Effects of Ancrod Anticoagulation on Renal Function in Sheep"; R. T. Olivet et al; Thrombosis Research, vol. 8: 673–682, 1976.

"The Use of Ancrod to Prevent Thromobsis on Prosthetic Heart Valves"; M. P. Singh; Thorax 25: 472–476, 1970.

"Characterization ofFibrin Degradation Products in Patients on Ancrod Therapy: Comparison with Fibrinogen Derivatives Produced by Plasmin"; C. Prentice et al; Br J Haemat. 27: 77–87, 1974.

Verh Dtsch. Gen Inn Med 79: 1397–1400, 1973; A. Ehrly et al; (Figure reproduced for Canadian product Monograph p. 15) on file at KP.

"Treatment of Experimental Venous Thrombosis with Streptokinase and Arvin (ARVIN)"; W. Pitney et al; Brit J Surg 58(6): 442–446, 1971.

Karas Clin. Cardiol. 14: 791–801 1991.

Hermans Am Heart J. 122(1 Pt 1): 171–187 1991.

Pollak et al. "Ancrod Causes Rapid Thrombolysis in Patients w/Acute Stroke" Am J Med Sci 299(5) 319–325 1990.

Cercek et al. "Ancrod Enhances The Thrombolytic Effect of Streptokinase & Urokinase" Thromb. Res. 47 417–426 1987.

Apprill et al. "Ancrod Decreases The Frequency of Cyclic Flow Variations & Causes Thrombolysis Following Acute Coronary Thrombosis" Am Heart J 113(4) 898–906 1987.

Bell "Defibringerating Enzymes" Hemostasis & Thrombosis 886–900 1987.

METHOD OF PREVENTING RESTENOSIS FOLLOWING CORONARY ANGIOPLASTY

BACKGROUND OF THE INVENTION

1. Field of the Invention

The present invention relates to methods of alleviating restenosis post-percutaneous transluminal coronary angioplasty (PTCA) or other coronary arterial intervention, and more particularly, to the use of ancrod to prevent restenosis in the coronary arteries.

2. Background of the Prior Art

Restenosis following PTCA is a significant limitation to the application of this otherwise useful revascularization technique. Restenosis occurs with varying frequency, and is generally accepted to be 25%–45%, depending on a number of factors including the site of the lesion, residual gradient post PTCA, sex (male), smoking and/or diabetes, skill of operator, method and timing of followup, and balloon size.

The problem typically manifests within 12 weeks to six months post procedure, and presents as recurrent angina in many cases, although "silent" restenosis occurs as well where ischemia recurs without overt clinical manifestation. This problem will become increasingly severe, as estimates that 400,000 or more procedures will be performed annually by the year 1993.

Clinical trials with other interventional methods such as atherectomy and intracoronary laser ablation suffer from the same restenosis problem, probably with similar frequencies of occurrence. Attempts to prevent restenosis with systemic drug therapy such as anti-platelet agents, anticoagulants, corticosteroids, and calcium channel blockers have uniformly failed to reduce its occurrence.

The histologic appearance of the recurrent lesion in restenosis is distinctly different from the atheromatous process of the original lesion. The atherosclerotic process evolves over many decades, beginning as flat, fatty streaks consisting of lipid-laden smooth muscle cells. Over time, these lesions evolve in complexity, becoming grossly fibrous plaques with ulceration, calcification, thrombosis and/or hemorrhage into the vessel wall. Microscopically, the atherosclerotic lesion has histological features of disruption and replication of the internal elastic lamina, spindle and smooth cell proliferation, interstitial fibrosis, intracellular and interstitial lipid accumulation, fibrin deposition, calcification, hemorrhage, thrombosis, capillary proliferation and macrophage infiltration. This process may be a response to injury. Most atherosclerotic lesions are endothelialized continuously with adjacent vascular endothelium.

The histopathology of restenosis after PTCA has been recently elucidated with the advent of percutaneous atherectomy procedures whereby such lesions are removed intact. In contrast to the atheromatous lesion, restenotic segments consist of a proliferation of cells and interstitial material resembling normal connective tissue with smooth muscle involvement. The lesion of restenosis thus differs distinctly from the original atherosclerotic disease both in time course of development and histologic appearance. It is likely that restenosis represents a zealous natural healing process of damaged coronary arterial walls with neointimal tissue impinging significantly on the vessel lumen.

If an agent or process could be found whereby restenosis could be significantly reduced or eliminated, a major advance in clinical care would be achieved. Savings of much morbidity, time, emotional investment, and economic cost could be realized by patients with coronary artery disease undergoing PTCA or other percutaneous coronary revascularization, in addition to improving patient safety.

SUMMARY OF THE INVENTION

The present invention has met the above-described needs by providing methods for reducing restenosis by the use of an effective amount of ancrod, a snake venom protein used as a defibrinogenating agent.

It is an object of the present invention to provide a method of reducing restenosis in coronary arteries.

It is another object of the present invention to provide a method of treating patients undergoing PTCA or other percutaneous coronary revascularization.

These and other objects of the present invention will be more fully understood from the following description of the invention.

DETAILED DESCRIPTION OF THE PREFERRED EMBODIMENTS

The present invention provides a method of reducing restenosis in coronary arteries by using an effective amount of ancrod. Ancrod is commercially available under the trademark ARVIN. In addition, the present invention provides a method of treating patients undergoing PTCA or other percutaneous coronary revascularization by an effective amount of ancrod.

Ancrod is a snake venom protein used as a defibrinogenating agent. Ancrod does not alter coagulation factors other than fibrinogen, nor does it induce serious bleeding.

While not wishing to be bound by any particular theory, it is believed that the proposed mechanism is that an early, space-occupying lesion after injury is composed chiefly of a fibrin/platelet/red blood cell thrombus. Because ancrod is a potent defibrinogenating/fibrinolytic agent, it is believed that ancrod-mediated reduction of lesion size early in the development of restenosis will result in a small final lesion.

Ancrod may be absorbed intramuscularly, subcutaneously, rectally and intraperitoneally. Ancrod may be administered parenterally, intravenously, subcutaneously, intramuscularly, rectally or orally by methods well know in the art.

The particular dosage regimen and schedule of ancrod administration is dependent on the aim of therapy. In any event, it is important to administer ancrod relatively slowly in order to prevent excessive coagulation.

For example, when thrombus formation is to be prevented, the intravenous route is preferred. Ancrod may be administered intravenously, for example, in a dosage unit of about 1 to 3 units (a unit is defined as the specific biological activity contained in 0.307 mg of the International Standard for ancrod) per kg of body weight, diluted with isotonic sodium chloride solution. Depending upon the fibrinogen level at the end of the initial infusion period, a similar second infusion in 50 mL of isotonic saline may be administered in order to achieve the desired fibrinogen level. In this example, the desired fibrinogen level to be achieved is about 100 mg/mL. Thereafter, maintenance doses may be administered after determining the patient's plasma fibrinogen concentration. In general, about 0.05 to about 1.5 u/kg of body weight diluted in 50 mL isotonic saline may be administered once or twice a day.

Ancrod may be administered subcutaneously in a dosage of about 0.3 to 4 units per kg of body weight. In this example, the desired fibrinogen level to be achieved is about 100 mg/dL. As with the intravenous route of administration, the number of doses and the intervals administered is dependent upon the patient's plasma fibrinogen level and response.

The use of ancrod for treatment of the above-mentioned condition may extend from 1 to 2 weeks for intravenous and 3 to 4 weeks for subcutaneous administration. However, depending upon patient response, a longer period of administration may be used.

The following examples serve to illustrate the invention and should in no way be construed as limiting the scope thereof.

EXAMPLE

An accurate model of this proliferative restenosis and obstructive neointima was developed in the coronary arteries of domestic crossbred swine, Sus scrofa. This model was developed in the Mayo Clinic Cardiac Laboratory in order that pharmacologic approaches to restenosis might be first tried in animals.

The advantage to using this model is that it is an accurate model of human restenosis, it utilizes the coronary arteries of swine (with known similarity to humans), and direct histopathologic correlation with therapy is readily assessed. Furthermore, results can be available within a short period of time. Schwartz et al., *Circulation*, vol 82(6), pps. 2190–2200 (1990).

The model utilizes severe coronary artery injury by a metallic coil implant with an oversized PTCA balloon. More specifically, metallic coils of either stainless steel or tantalum were implanted into the media of pig coronary arteries using oversized balloons and high inflation pressures. (0.125 mm stainless steel or tantalum wire coils implanted percutaneously in pig coronary arteries with oversized PTCA balloons inflated to 14 atm).

In all pigs studied at necropsy a substantial proliferative response was observed, and the histological appearance of the proliferative tissue was identical to that in human specimens obtained via atherectomy in post PTCA restenosis cases.

The study showed that ancrod can successfully inhibit the restenotic response to injury in a porcine model of human restenosis. Specifically, quantitative measurements of luminal stenosis and proliferative response in treated and untreated groups of pigs were used to determine inhibition of restenosis.

The lesions were seen at time intervals of 11 days minimum to 42 days. Typically, 28 days were required to generate these lesions.

In some animals, some proliferative tissue was noted, but not to the same severe degree of tight luminal stenosis. Histology typically showed less vessel damage in these specimens, without rupture of the internal elastic lamina. The results indicate that coil oversizing and high balloon implant pressures (up to 14 atm) should be used. Severe stenotic lesions are reliably generated.

Concern for the efficacy and practicality of ancrod in the pig motivated a preliminary study of the ability of ancrod to defibrinogenate this animal. Two animals were used, both of which received a 70u intravenous administration over 10 minutes. Measures of clotting (thrombin time, activated clotting time, APTT) are shown in the following table.

|  | ACT (sec) | Thrombin Time (sec) | Protime (sec) | APTT (sec) | Fibrinogen (mg %) |
|---|---|---|---|---|---|
| Pig #728 | | | | | |
| Pre | 149 | 40 | 11 | 26 | 420 |
| 30 min |  | >600 | *** | *** | 184 |
| 1 hour | 112 | >600 | 26 | 33 | 0 |
| 2 hr | 192 | — | — | — | — |
| 4 hr | >1500 | >600 | — | — | 0 |
| 24 hr |  | 17 | 11 | — | 361 |
| Pig #733 | | | | | |
| Pre | 58 | 32 | 10 | 25.5 | 586 |
| 30 min | 90 | >600 | *** | *** | 397 |
| 1 hr | 129 | >600 | 11.5 | 62 | 204 |
| 4 hr | 156 | >600 | 18 | 35 | 0 |
| 24 hr | 92 | 21 | 12 | 61 | 319 |

The data in this table clearly show the defibrinogenation effects in the two pigs which receiving the ancrod. The *** symbols indicate that immediate clot formed upon addition of calcium to the plasma. The dash (—) above indicates not measured.

After these studies, each animal appeared to suffer no ill effects from the relatively rapid infusion. These results demonstrate that ancrod is effective in safely defibrinogenating the pig.

Cutdown was performed on the ventral neck, with isolation of the right external carotid artery and internal jugular vein. The internal jugular vein was cannulated and an indwelling catheter (polyethylene 0.060") placed in the superior vena cava. This catheter was attached to an implantable infusion pump which has been filled with ancrod 700 units. An arterial hemostatic sheath was placed in the carotid artery for access to the coronary tree.

The method of metallic coil implantation to generate neointimal hyperplasia and proliferation in young domestic crossbred pigs is a procedure which can now be accomplished with comparative ease and efficiency. The pig model has been chosen since their large and small vessel coronary anatomy is comparable to humans, their coagulation system resembles the human system, and because the neointimal hyperplasia resulting from coil implantation is identical to human tissue found post PTCA in restenosis.

For this study there were 10 pigs in each group, ancrod treated and untreated Assuming an accidental death rate of 20% 4 extra pigs were requested (24 total).

After insuring adequate hemostasis (cautery and silver nitrate) from cutdown, a custom-curved PTCA guide catheter was advanced to the aortic root and the left main coronary artery engaged under fluoroscopic guidance. Metal coils were implanted in at least 2 predetermined coronary arteries of the animal, so that at least 20 lesions in each group were available for study.

Animals were randomized to either treated or untreated groups.

All animals received 1) a single oral dose of sustained released verapamil (commercially available from Knoll Pharmaceutical Company, Whippany, N.J. as Isoptin®SR) 120 mg one day prior to coil implant; and 2) oral aspirin 650 mg 1 day prior to coil implant and continuing for the 10 day period of ancrod infusion after implant.

The verapamil was used to reduce coronary artery spasm during implant. Aspirin has been shown to reduce platelet aggregation acutely, and to increase survival rate without affecting the degree of neointimal proliferation.

The treatment group received ancrod intravenously 70 units (about 2 units/Kg) over 1 hour during the cutdown procedure. As noted, the continuous infusion osmotic pump contained ancrod, 700 units infused continuously at about 70 units/day into the superior vena cava. Fibrinogen levels were monitored to assess efficacy and adequate dose of ancrod. For the untreated group, the same procedure was followed except the pump contained normal saline only.

The parameters below were measured daily for 3 days, then every 3 days thereafter for 10 days.

All animals were sacrificed at 28 +/− days for histopathologic examination and quantification. The animals were sacrificed using a commercial intravenous euthanasia solution ("Sleepaway") as approved by the Mayo clinic section of Veterinary Medicine. The heart was removed and placed on a fixation pump under pressure. Formalin 10% was the fixation medium.

The left atrial appendage was removed for access to the proximal left coronary artery system. The coronary artery segments with coils were dissected free of the epicardium. The segment containing the coil was isolated allowing enough tissue to contain uninvolved vessel at either end.

These arterial segments, each roughly 2.5 cm in length, were sectioned grossly with a scalpel by transverse cuts 3 mm apart. The cut wire coil was removed via forceps after gross photography of each 3 mm section.

The 3 mm sections with coils removed was imbedded and stained with hematoxylin and eosin, and elastin stains. These sections were observed with quantitative low and high power light microscopy where a movable calibrated reticle was utilized for making length measurements in the plane of microscopic view. Each section was be photographed with both high and low power visualization. This allowed for observation of the normal vessel, progressing into proliferative vessel where the coil was located, and back to the normal vessel beyond the point where the coil was located.

Quantitative measurement of the degree of proliferation was assessed by three methods: 1) maximum, minimum, and mean thickness of neointimal tissue; 2) maximum percent luminal stenosis; and 3) medial thickness. Measurements were done via calibrated microscope reticle.

Neointimal proliferative area was calculated by assuming the native and residual lumina to be prolate ellipses. A major and minor axis was measured, and area calculated by the expression:

$$\text{Area} = \pi \times \text{Major Axis}/2 \times \text{Minor Axis}/2.$$

Mean neointimal thickness was calculated by measuring proliferative thickness at each wire site and dividing by the number of wires present in that section.

Quantitative maximum percent area stenosis was calculated according to the following expression:

$$\text{Percent (\%) Stenosis} = 100 \times (1 - \text{stenotic area/native area}).$$

Maximum medial thickness was also measured.

All three parameters of neointimal area, maximum percent stenosis, and mean neointimal smooth muscle cell density were compared between the treated group and the control group.

Pathologic lesions in 5 of 5 implanted animals (at 11 days to 63 days) included a severe proliferative response of medial smooth muscle cells with significant luminal compromise (mean area stenosis 70%+/−24% SD). Disruption of the internal elastic lamina was present in all vessels showing the proliferative response, as was mild chronic inflammation surrounding the wire itself. One animal died spontaneously at 11 days from a tight, proliferative left anterior descending coronary artery (LAD) stenosis. In all animals, histopathologic features of the proliferative neointimal tissue were identical to those of human restenotic tissue post PTCA obtained in 38 patients by atherectomy.

Whereas particular embodiments of the invention have been described above for purposes of illustration, it will be appreciated by those skilled in the art that numerous variations of the details may be made without departing from the invention as described in the appended claims.

What is claimed is:

1. A method of reducing restenosis in coronary arteries of a patient following percutaneous coronary arterial intervention comprising administering to said patient, post-coronary arterial intervention, a restenosis reducing effective amount of ancrod.

2. The method of claim 1 wherein ancrod is administered parenterally, intravenously, subcutaneously, intramuscularly, rectally or orally.

3. The method of claim 2 wherein ancrod is administered intravenously.

4. A method of treating percutaneous transluminal coronary angioplasty (PTCA) patients to reduce restenosis in coronary arteries comprising administering to patients in need of said treatment post-PTCA a restenosis reducing effective amount of ancrod.

5. The method of claim 4 wherein ancrod is administered parenterally, intravenously, subcutaneously, intramuscularly, rectally or orally.

6. The method of claim 5 wherein ancrod is administered intravenously.

7. A method of treating patients undergoing percutaneous coronary revascularization to reduce restenosis comprising administering to patients in need of said treatment a restenosis-reducing effective amount of ancrod.

8. A method as in claim 7, wherein ancrod is administered parenterally, intravenously, subcutaneously, intramuscularly, rectally or orally.

9. A method as in claim 1, 4 or 7, wherein ancrod is administered intravenously in a dosage of about 1 to 3 units per kg of body weight.

10. A method as in claim 9, wherein ancrod is administered to achieve a fibrinogen level of about 100 mg/mL.

11. A method as in claim 1, 4 or 7, ancrod is administered subcutaneously in a dosage of about 0.3 to 4 units per kg of body weight.

12. A method as in claim 11, wherein ancrod is administered to obtain fibrinogen level of about 100 mg/dL.

* * * * *